United States Patent
Weismantel et al.

(10) Patent No.: US 7,915,355 B2
(45) Date of Patent: Mar. 29, 2011

(54) POLYMERIZATION PROCESS

(75) Inventors: Matthias Weismantel, Jossgrund-Oberndorf (DE); Michael de Marco, Weinheim (DE); Andreas Daiss, Deidesheim (DE); Dominicus van Esbroeck, Nanjing (CN); Karl J. Possemiers, Gravenwezel (BE); Ronny De Kaey, Mortsel (BE); Leo Van Miert, Kapellen (BE)

(73) Assignee: BASF SE, Ludwigshafen (DE)

( * ) Notice: Subject to any disclaimer, the term of this patent is extended or adjusted under 35 U.S.C. 154(b) by 322 days.

(21) Appl. No.: 12/065,358

(22) PCT Filed: Aug. 31, 2006

(86) PCT No.: PCT/EP2006/065846
§ 371 (c)(1),
(2), (4) Date: Feb. 29, 2008

(87) PCT Pub. No.: WO2007/028749
PCT Pub. Date: Mar. 15, 2007

(65) Prior Publication Data
US 2008/0275195 A1  Nov. 6, 2008

(30) Foreign Application Priority Data
Sep. 7, 2005 (DE) .......... 10 2005 042 608

(51) Int. Cl.
*C08F 2/00*  (2006.01)
*C08F 2/01*  (2006.01)
*C08F 20/06*  (2006.01)
*C08F 120/06*  (2006.01)

(52) U.S. Cl. ............ 526/88; 526/62; 526/64; 526/317.1

(58) Field of Classification Search .................... 526/62, 526/64, 88
See application file for complete search history.

(56) References Cited

U.S. PATENT DOCUMENTS

| 3,316,199 | A | * | 4/1967 | Murphy .................. 524/461 |
| 4,402,914 | A | | 9/1983 | Eckhoff |
| 6,455,600 | B1 | * | 9/2002 | Hahnle et al. ............ 521/63 |
| 6,667,372 | B1 | * | 12/2003 | Miyake et al. ............ 526/61 |
| 6,710,141 | B1 | | 3/2004 | Heide et al. |
| 6,727,345 | B2 | | 4/2004 | Kajikawa et al. |
| 6,911,499 | B1 | | 6/2005 | Brehm et al. |
| 2003/0020199 | A1 | | 1/2003 | Kajikawa et al. |
| 2004/0014901 | A1 | | 1/2004 | Heide et al. |
| 2004/0092688 | A1 | * | 5/2004 | Dairoku et al. ........... 526/317.1 |

FOREIGN PATENT DOCUMENTS

| EP | 0 315 185 | 5/1989 |
| EP | 0 780 424 | 6/1997 |
| GB | 837 974 | 6/1960 |
| GB | 1 225 764 | 3/1971 |
| TW | 242534 B1 * | 11/2005 |
| WO | WO-01/16197 | 3/2001 |
| WO | WO-01/38402 | 5/2001 |
| WO | WO-02/32964 | 4/2002 |
| WO | WO-03/004237 | 1/2003 |
| WO | WO-03/022896 | 3/2003 |

OTHER PUBLICATIONS

Chaun et al; English abstract of TW 242534 B1; Nov. 2005.*
International Search Report in PCT/EP2006/065846 dated Nov. 28, 2006.
Ullmann et al., *Ullmann's Encyclopedia of Industrial Chemistry*, 6th ed., vol. 35, pp. 1-21, New York: Wiley, 2005.

* cited by examiner

*Primary Examiner* — Vasu Jagannathan
*Assistant Examiner* — Karuna P Reddy
(74) *Attorney, Agent, or Firm* — Marshall, Gerstein & Borun LLP

(57) ABSTRACT

The present invention relates to a process for continuously preparing water-absorbing polymers by mixing a monomer solution with at least one crosslinker and polymerizing the resulting mixture, wherein the residence time of the mixture between the addition of the at least one crosslinker and the entry into the polymerization reactor is less than 180 seconds, and also to an apparatus for performing the process.

19 Claims, 1 Drawing Sheet

POLYMERIZATION PROCESS

CROSS-REFERENCE TO RELATED APPLICATIONS

Figure 1:
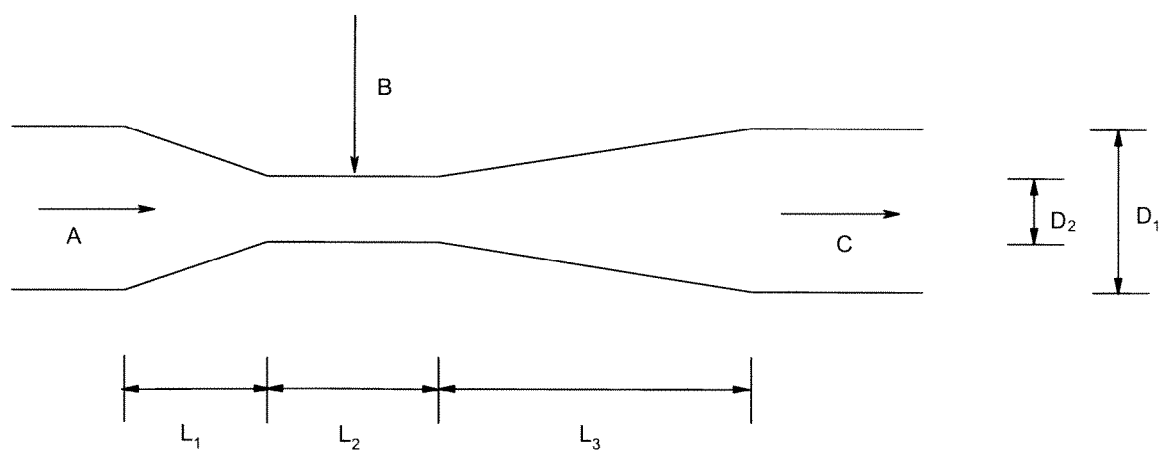

This is the U.S. national phase application of International Application No. PCT/EP2006/065846, filed Aug. 31, 2006, which claims the benefit of German patent application No. 10 2005 042 608.5, filed Sep. 7, 2005.

The present invention relates to a process for continuously preparing water-absorbing polymers by mixing a monomer solution with at least one crosslinker and polymerizing the resulting mixture, wherein the residence time of the mixture between the addition of the at least one crosslinker and the entry into the polymerization reactor is less than 180 seconds, and also to an apparatus for performing the process.

Further embodiments of the present invention can be taken from the claims, the description and the examples. It is evident that the features of the inventive subject matter which have been mentioned above and will be explained below are usable not only in the combination specified in each case but also in other combinations without leaving the scope of the invention.

Water-absorbing polymers are especially polymers of (co) polymerized hydrophilic monomers, graft (co)polymers of one or more hydrophilic monomers on a suitable graft base, crosslinked cellulose ethers or starch ethers, crosslinked carboxymethylcellulose, partly crosslinked polyalkylene oxide or natural products swellable in aqueous liquids, for example guar derivatives, preference being given to water-absorbing polymers based on partly neutralized acrylic acid. Such polymers are used as products that absorb aqueous solutions to produce diapers, tampons, sanitary napkins and other hygiene articles, but also as water-retaining agents in market gardening.

The preparation of the water-absorbing polymers is described, for example, in the monograph "Modern Superabsorbent Polymer Technology", F. L. Buchholz and A. T. Graham, Wiley-VCH, 1998, or in Ullmann's Encyclopedia of Industrial Chemistry, 6th Edition, Volume 35, pages 73 to 103. The preferred preparation process is solution or gel polymerization. In this technology, a monomer mixture is firstly prepared and is neutralized batchwise and then transferred to a polymerization reactor, or initially charged actually within the polymerization reactor. In the batchwise or continuous process which follows, the reaction is effected to give the polymer gel which, in the case of a stirred polymerization, is already in comminuted form. The polymer gel is subsequently dried, ground and sieved and then transferred to further surface treatment.

A continuous polymerization process forms the basis, for example, of WO-A-01/38402, in which the aqueous monomer solution together with the initiator and the inert gas is fed continuously to a mixing kneader with at least two axially parallel-rotating shafts.

Continuous gel polymerizations are also known from WO-A-03/004237, WO-A-03/022896 and WO-A-01/016197.

It was an object of the present invention to provide an improved polymerization process for preparing crosslinked polymers, in which the crosslinker conversion should be at a maximum and the proportion of uncrosslinked polymers should be at a minimum.

The object is achieved by a process for continuously preparing water-absorbing polymers by mixing a monomer solution with at least one crosslinker and polymerizing the resulting mixture, wherein the residence time of the mixture between the addition of the at least one crosslinker and the entry into the polymerization reactor is less than 180 seconds.

The residence time of the mixture between the addition of the at least one crosslinker and the entry into the polymerization reactor is preferably less than 120 seconds, preferentially less than 60 seconds, more preferably less than 30 seconds, most preferably less than 10 seconds. A very particularly advantageous residence time is in the range from 1 to 5 seconds.

The polymerization tendency can be reduced when the connection between crosslinker metering and polymerization reactor at least partly, preferably at least to an extent of at least 50% of the surface, more preferably as completely as possible in construction terms, has a material surface which has a contact angle for water of at least 60°, preferably at least 90°, more preferably at least 100°.

The contact angle is a measure of the wetting behavior and can be measured by customary methods, preferably according to DIN 53900.

Suitable materials with corresponding wetting behavior are polyethylene, polypropylene, polyester, polyamide, polytetrafluoroethylene, polyvinyl chloride, epoxy resins and silicone resins. Very particular preference is given to polypropylene.

The process according to the invention is particularly advantageous when the crosslinker, depending on the type and amount, is not completely soluble in the monomer solution and is present at least partly in dispersed form in the monomer solution. The presence of a dispersion can be determined readily by scattered light measurements.

The viscosity of the monomer solution at 15° C. is preferably from 5 to 200 mPas, more preferably from 10 to 100 mPas, most preferably from 20 to 50 mPas, the viscosity being measured with a Brookfield viscometer (spindle 2, 100 rpm).

The monomer concentration in the monomer solution is preferably from 10 to 80% by weight, more preferably from 20 to 60% by weight, most preferably from 30 to 50% by weight.

The monomer solution comprises at least one monoethylenically unsaturated monomer, preferably acrylic acid and/or salts thereof. The proportion of acrylic acid and/or salts thereof in the total amount of monomer is preferably at least 50 mol %, more preferably at least 90 mol %, most preferably at least 95 mol %.

In a preferred embodiment of the present invention, the at least one crosslinker is metered in via a Venturi tube.

A Venturi tube is a tube constriction of restricted length, in which the pressure drop is converted substantially reversibly to kinetic energy. To this end, the cross-sectional area $F_1$ is reduced over the distance $L_1$ (narrowing zone) to the cross section $F_2$, the cross-sectional area $F_2$ is kept constant over the distance $L_2$ (constriction zone) and the cross-sectional area $F_2$ is then widened again over the distance $L_3$ (diffuser) to the cross-sectional area $F_1$. The cross-sectional area $F_1$ is greater than the cross-sectional area $F_2$ and the length $L_3$ greater than the length $L_1$.

The crosslinker is metered in preferably in the region of the zone $L_1$ or of the zone $L_2$.

FIG. 1 shows a typical Venturi tube, the reference symbols having the following meaning:
A: monomer solution before metering of crosslinker
B: crosslinker feed
C: monomer solution comprising crosslinker
$L_1$: narrowing zone
$L_2$: constriction zone
$L_3$: diffuser $D_1$: diameter of the pipeline
$D_2$: diameter of the constriction zone The optimal design of a Venturi tube is known per se to those skilled in the art. The Venturi tube is preferably designed such that the pressure in the region of the zone $L_2$ is less than the ambient pressure (suction conveying) and/or that the flow in the region of the zone $L_2$ is turbulent, and the Reynolds number should be at least 1000, preferably at least 2000, more preferably at least 3000, most preferably at least 4000, and typically less than 10 000 000.

The at least one crosslinker can be metered in via one or more addition points.

For example, the reactants can be metered in via two, three, four, five or six addition points, in which case the addition points are preferably arranged such that they have a common axis (for two addition points) or form a symmetrical star (for at least three addition points) and the axis or star is at right angles to the flow direction of the monomer solution (multiple addition points).

The division into a plurality of addition points brings about more uniform mixing.

When a plurality of crosslinkers is used, they may be metered in separately or as a mixture.

It is also possible to mix the at least one crosslinker first with a portion of the monomer solution and then to mix this mixture with the majority of the monomer solution.

Preference is given to mixing a preneutralized monomer solution with the at least one crosslinker, inertizing the mixture, mixing the inertized mixture with an initiator and polymerizing.

The water-absorbing polymers are obtained, for example, by polymerization of a monomer solution comprising
a) at least one ethylenically unsaturated acid-functional monomer,
b) at least one crosslinker,
c) if appropriate one or more ethylenically and/or allylically unsaturated monomers copolymerizable with the monomer a), and
d) if appropriate one or more water-soluble polymers onto which the monomers a), b) and if appropriate c) can be at least partly grafted.

Suitable monomers a) are, for example, ethylenically unsaturated carboxylic acids, such as acrylic acid, methacrylic acid, maleic acid, fumaric acid and itaconic acid, or derivatives thereof, such as acrylamide, methacrylamide, acrylic esters and methacrylic esters. Particularly preferred monomers are acrylic acid and methacrylic acid. Very particular preference is given to acrylic acid.

The monomers a), especially acrylic acid, comprise preferably up to 0.025% by weight of a hydroquinone monoether. Preferred hydroquinone monoethers are hydroquinone monomethyl ether (MEHQ) and/or tocopherols.

Tocopherol refers to compounds of the following formula:

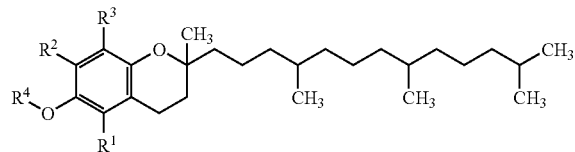

where $R^1$ is hydrogen or methyl, $R^2$ is hydrogen or methyl, $R^3$ is hydrogen or methyl and $R^4$ is hydrogen or an acyl radical having from 1 to 20 carbon atoms.

Preferred $R^4$ radicals are acetyl, ascorbyl, succinyl, nicotinyl and other physiologically tolerable carboxylic acids. The carboxylic acids may be mono-, di- or tricarboxylic acids.

Preference is given to alpha-tocopherol where $R^1$=$R^2$=$R^3$=methyl, especially racemic alpha-tocopherol. $R^1$ is more preferably hydrogen or acetyl. Especially preferred is RRR-alpha-tocopherol.

The monomer solution comprises preferably not more than 130 ppm by weight, more preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having an appropriate hydroquinone monoether content.

The crosslinkers b) are compounds having at least two polymerizable groups which can be free-radically polymerized into the polymer network. Suitable crosslinkers b) are, for example, ethylene glycol dimethacrylate, diethylene glycol diacrylate, allyl methacrylate, trimethylolpropane triacrylate, triallylamine, tetraallyloxyethane, as described in EP-A-0 530 438, di- and triacrylates, as described in EP-A-0 547 847, EP-A-0 559 476, EP-A-0 632 068, WO-A-93/21237, WO-A-03/104299, WO-A-03/104300, WO-A-03/104301 and DE-A-103 31 450, mixed acrylates which, as well as acrylate groups, comprise further ethylenically unsaturated groups, as described in DE-A-103 31 456 and WO-A-04/013064, or crosslinker mixtures as described, for example, in DE-A-195 43 368, DE-A-196 46 484, WO-A-90/15830 and WO-A-02/32962.

Suitable crosslinkers b) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl(meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described, for example, in EP-A-0 343 427. Suitable crosslinkers b) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. In the process of the invention, it is possible to use di(meth)acrylates of polyethylene glycols, the polyethylene glycol used having a molecular weight between 300 and 1000.

However, particularly advantageous crosslinkers b) are di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol or of 3-tuply propoxylated trimethylolpropane, and also of 3-tuply mixed ethoxylated or propoxylated glycerol or of 3-tuply mixed ethoxylated or propoxylated trimethylolpropane, of 15-tuply ethoxylated glycerol, of 15-tuply ethoxylated trimethylolpropane, of 40-tuply ethoxylated glycerol, of 40-tuply ethoxylated trimethylolethane or of 40-tuply ethoxylated trimethylolpropane.

Very particularly preferred crosslinkers b) are polyethoxylated and/or -propoxylated glycerols which have been esterified with acrylic acid or methacrylic acid to di- or triacrylates, as described, for example, in WO 03/104301. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels (typically below 10 ppm by weight) in the water-absorbing polymer and the aqueous extracts of the water-absorbing polymers produced therewith have an almost unchanged surface tension (typically not less than 0.068 N/m) compared with water at the same temperature.

The amount of crosslinker b) is preferably from 0.01 to 1% by weight, more preferably from 0.05 to 0.5% by weight, most preferably from 0.1 to 0.3% by weight, obtained in each case on the monomer a).

Examples of ethylenically unsaturated monomers c) which are copolymerizable with the monomers a) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers d) include polyvinyl alcohol, polyvinylpyrrolidone, starch, starch derivatives, polyglycols or polyacrylic acids, preferably polyvinyl alcohol and starch.

For optimal action, the preferred polymerization inhibitors require dissolved oxygen. Typically, the monomer solutions are substantially freed of oxygen before the polymerization (inertization), for example by means of flowing an inert gas, preferably nitrogen, through them. This distinctly weakens the action of the polymerization inhibitors. The oxygen content of the monomer solution is preferably lowered to less than 1 ppm by weight and more preferably to less than 0.5 ppm by weight before the polymerization.

The preparation of a suitable base polymer and also further suitable hydrophilic ethylenically unsaturated monomers d) are described in DE-A-199 41 423, EP-A-0 686 650, WO-A-01/45758 and WO-A-03/104300.

Water-absorbing polymers are typically obtained by addition polymerization of an aqueous monomer solution and, if appropriate, subsequent comminution of the hydrogel. Suitable preparation methods are described in the literature. Water-absorbing polymers are obtainable, for example, by
- gel polymerization in the batch process or tubular reactor and subsequent comminution in meat grinder, extruder or kneader (EP-A-0 445 619, DE-A-19 846 413)
- addition polymerization in kneader with continuous comminution by contrarotatory stirring shafts for example (WO-A-01/38402)
- addition polymerization on belt and subsequent comminution in meat grinder, extruder or kneader (DE-A-38 25 366, U.S. Pat. No. 6,241,928)
- emulsion polymerization, which produces bead polymers having a relatively narrow gel size distribution (EP-A-0 457 660)
- in situ addition polymerization of a woven fabric layer which, usually in a continuous operation, has previously been sprayed with aqueous monomer solution and subsequently been subjected to a photopolymerization (WO-A-02/94328, WO-A-02/94329).

The reaction is preferably carried out in a kneader, as described, for example, in WO-A-01/38402, or on a belt reactor, as described, for example, in EP-A-0 955 086.

Neutralization can also be carried out partly after the polymerization, at the hydrogel stage. It is therefore possible to neutralize up to 40 mol %, preferably from 10 to 30 mol % and more preferably from 15 to 25 mol % of the acid groups before the polymerization by adding a portion of the neutralizing agent to the monomer solution and setting the desired final degree of neutralization only after the polymerization, at the hydrogel stage. The monomer solution can be neutralized by mixing in the neutralizing agent. The hydrogel may be comminuted mechanically, for example by means of a meat grinder, in which case the neutralizing agent can be sprayed, sprinkled or poured on and then carefully mixed in. To this end, the gel mass obtained can be repeatedly ground in the meat grinder for homogenization. Neutralization of the monomer solution to the final degree of neutralization is preferred.

The neutralized hydrogel is then dried with a belt or drum dryer until the residual moisture content is preferably below 15% by weight and especially below 10% by weight, the water content being determined by EDANA (European Disposables and Nonwovens Association) recommended test method No. 430.2-02 "Moisture content". If desired, drying can also be carried out using a fluidized bed dryer or a heated plowshare mixer. To obtain particularly white products, it is advantageous to dry this gel while ensuring rapid removal of the evaporating water. To this end, the dryer temperature must be optimized, the air feed and removal has to be controlled, and sufficient venting must be ensured in each case. The higher the solids content of the gel, the simpler the drying, by its nature, and the whiter the product. The solids content of the gel before the drying is therefore preferably between 30% and 80% by weight. It is particularly advantageous to vent the dryer with nitrogen or another nonoxidizing inert gas. If desired, however, it is possible simply just to lower the partial pressure of the oxygen during the drying in order to prevent oxidative yellowing processes. In general, though, adequate venting and removal of the water vapor also still lead to an acceptable product. A very short drying time is generally advantageous with regard to color and product quality.

The dried hydrogel is preferably ground and sieved, useful grinding apparatus typically including roll mills, pin mills or swing mills. The particle size of the sieved, dry hydrogel is preferably below 1000 μm, more preferably below 900 μm and most preferably below 800 μm, and preferably above 100 μm, more preferably above 150 μm and most preferably above 200 μm.

Very particular preference is given to a particle size (sieve cut) of from 106 to 850 μm. The particle size is determined according to EDANA (European Disposables and Nonwovens Association) recommended test method No. 420.2-02 "Particle size distribution".

The base polymers are then preferably surface postcrosslinked. Postcrosslinkers suitable for this purpose are compounds comprising two or more groups capable of forming covalent bonds with the carboxylate groups of the hydrogel. Suitable compounds are, for example, alkoxysilyl compounds, polyaziridines, polyamines, polyamidoamines, di- or polyglycidyl compounds, as described in EP-A-0 083 022, EP-A-543 303 and EP-A-937 736, di- or polyfunctional alcohols, as described in DE-C-33 14 019, DE-C-35 23 617 and EP-A-450 922, or β-hydroxyalkylamides, as described in DE-A-102 04 938 and U.S. Pat. No. 6,239,230.

In addition, DE-A-40 20 780 describes cyclic carbonates, DE-A-198 07 502 2-oxazolidone and its derivatives, such as 2-hydroxyethyl-2-oxazolidone, DE-A-198 07 992 bis- and poly-2-oxazolidinones, DE-A-198 54 573 2-oxotetrahydro-1,3-oxazine and its derivatives, DE-A-198 54 574 N-acyl-2- oxazolidones, DE-A-102 04 937 cyclic ureas, DE-A-103 34 584 bicyclic amide acetals, EP-A-1 199 327 oxetanes and cyclic ureas and WO-A-03/031482 morpholine-2,3-dione and its derivatives, as suitable surface postcrosslinkers.

The postcrosslinking is typically carried out in such a way that a solution of the surface postcrosslinker is sprayed onto the hydrogel or onto the dry base polymer powder. After the spraying, the polymer powder is dried thermally, and the crosslinking reaction may take place either before or during drying.

The spraying with a solution of the crosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Suitable mixers are, for example, Lödige® mixers, Bepex® mixers, Nauta® mixers, Processall® mixers and Schugi® mixers.

The thermal drying is preferably carried out in contact dryers, more preferably shovel dryers and most preferably disk dryers. Suitable dryers are, for example, Bepex® dryers and Nara® dryers. It is also possible to use fluidized bed dryers.

The drying can be effected in the mixer itself, by heating the jacket or blowing in warm air. It is equally possible to use a downstream dryer, for example a tray dryer, a rotary tube oven or a heatable screw. It is also possible, for example, to utilize an azeotropic distillation as a drying process.

Preferred drying temperatures are in the range from 50 to 250° C., preferably in the range from 50 to 200° C. and more preferably in the range from 50 to 150° C. The preferred residence time at this temperature in the reaction mixer or dryer is below 30 minutes and more preferably below 10 minutes.

The process according to the invention enables the economically viable continuous preparation of postcrosslinked water-absorbing polymer particles. The crosslinkers used are utilized efficiently. The proportion of unconverted crosslinkers and of un-crosslinked polymers is particularly low.

The present invention further provides an apparatus for the performance of the process according to the invention, comprising
i) a polymerization reactor,
ii) at least one inlet to the polymerization reactor i),
iii) at least one Venturi tube in the inlet ii) and
iv) at least one inlet to the Venturi tube iii),
the inlet iv) opening into the Venturi tube iii), preferably into the narrowing zone.

Advantageously, the inner surface of the inlet ii) between polymerization reactor i) and inlet iii) at least partly has a contact angle for water of at least 60°, preferably at least 90°, more preferably at least 100°.

The contact angle is a measure of the wetting behavior and can be measured by customary methods, preferably according to DIN 53900.

Suitable materials with corresponding wetting behavior are polyethylene, polypropylene, polyester, polyamide, polytetrafluoroethylene, polyvinyl chloride, epoxy resins and silicone resins. Very particular preference is given to polypropylene.

The length of the inlet ii) between polymerization reactor i) and inlet iii) is preferably from 0.5 to 20 m, more preferably from 1 to 10 m, most preferably from 1.5 to 5 m.

The cross-sectional area of the inlet ii) is preferably from 10 to 1000 cm$^2$, more preferably from 25 to 500 cm$^2$, most preferably from 50 to 200 cm$^2$. The inlet ii) preferably has a circular cross section.

Preferably at least two inlets iii) are present, more preferably two, three, four, five or six inlets iii), the inlets iii) preferably being arranged such that they have a common axis (for two inlets) or form a symmetrical star (for at least three inlets), and the axis or star is at right angles to the flow direction of the monomer solution (multiple addition points).

Particularly advantageously, two, three or four multiple addition points are arranged in succession.

For example, at least eight inlets iii) may be present, in which case four inlets iii) open in a cross shape into the monomer line; the at least 2 groups of four inlets iii) being arranged in succession and offset relative to one another.

In a preferred embodiment, the inlets iii) are arranged such that the angle between the inlet ii) and the inlet iii) in flow direction is less than 90°. The angle is preferably from 10 to 80°, more preferably from 20 to 70°, most preferably from 30 to 60°.

The apparatus is preferably free of dead spaces and the surfaces should have minimum roughness.

Dead spaces are sections of the apparatus in which the average residence time is increased in the course of operation as intended.

The inventive apparatus is outstandingly suitable for metering crosslinkers into monomer solutions. Especially owing to their specific inner surface, the polymerization tendency is low.

Methods:

The measurements should, unless stated otherwise, be carried out at an ambient temperature of 23±2° C. and a relative humidity of 50±10%. The water-absorbing polymers are mixed thoroughly before the measurement.

Residual Crosslinkers

The content of residual crosslinkers of the water-absorbing polymer particles is determined by means of HPLC using a ZORBAX® Eclipse XDB C18 reverse-phase column (Agilent Technologies, US) with downstream UV/VIS detection and calibration with external standard. The mobile phase used is acetonitrile/water with a gradient.

Extractables

The content of extractables in the water-absorbing polymer particles is determined in accordance with the EDANA (European Disposables and Nonwovens Association) recommended test method No. 470.2-02 "Extractables".

The EDANA test methods are obtainable, for example, from the European Disposables and Nonwovens Association, Avenue Eugene Plasky 157, B-1030 Brussels, Belgium.

EXAMPLES

Example 1

Continuous mixing of water, 50% by weight sodium hydroxide solution and acrylic acid prepared a 38.8% by weight acrylic acid/sodium acrylate solution with a degree of neutralization of 71.3 mol %. As the components were mixed, the monomer solution was cooled to a temperature of 29° C. continuously by a heat exchanger.

The polyethylenically unsaturated crosslinker used was polyethylene glycol diacrylate (diacrylate of a polyethylene glycol having a mean molar mass of 400 g/mol). The amount used was 2 kg per t of monomer solution. The crosslinker was metered in via one addition point. The addition was effected via a pipeline having a diameter of 0.5 cm. The addition point of the crosslinker was 1 m upstream of the reactor entrance. The residence time of the crosslinker in the monomer solution upstream of the polymerization reactor was 1.5 seconds.

After the crosslinker, hydrogen peroxide and sodium peroxodisulfate were metered into the monomer solution. The amounts used per t of monomer solution were 1.0 kg of 0.25% by weight hydrogen peroxide and 3.1 kg of 15% by weight aqueous sodium peroxodisulfate.

The throughput of the monomer solution was 18 t/h.

The monomer mixture and ascorbic acid were metered continuously into a List Contiknet reactor (from List, Arisdorf, Switzerland). The pressure in the reactor was increased by 10 mbar relative to the environment. The amount of 1% by weight aqueous ascorbic acid used was 1.1 kg per t of monomer solution.

Before being fed in, the reaction solution was degassed with nitrogen and had a temperature of 23.5° C. at the feed. The reactor was operated with a rotational speed of the shafts of 38 rpm. The residence time of the reaction mixture in the reactor was 15 minutes.

After polymerization had ended and gel comminution, the polymer gel was placed onto a belt dryer. During the drying, a pressure reduced by 5 mbar relative to ambient pressure was set. The precomminuted polymer gel was placed onto the belt dryer with a layer thickness of 10 cm and dried with warm air (175° C.). The residence time in the belt dryer was 37 minutes.

The resulting polymer powder was ground, sieved (from 100 to 800 μm) and surface postcrosslinked.

The postcrosslinker used was a 1.2% by weight solution of ethylene glycol digycidyl ether in propylene glycol/water (1:2). Based on the polymer powder, 5% by weight of postcrosslinker solution were sprayed on and the polymer powder was aftertreated thermally at 150° C. for 60 minutes.

The postcrosslinked polymer powder was analyzed. The results are compiled in Table 1.

Example 2

The procedure of Example 1 was repeated. The addition point of the crosslinker was 3.5 m upstream of the reactor entrance. The residence time of the crosslinker in the monomer solution upstream of the polymerization reactor was 5.3 seconds.

The postcrosslinked polymer powder was analyzed. The results are compiled in Table 1.

Example 3

The procedure of Example 1 was repeated. The addition point of the crosslinker was 2.5 m upstream of the reactor entrance. The residence time of the crosslinker in the monomer solution upstream of the polymerization reactor was 3.8 seconds.

The postcrosslinked polymer powder was analyzed. The results are compiled in Table 1.

TABLE 1

| | Residence time of the crosslinker | | |
| --- | --- | --- | --- |
| Example | Residence time | Extractables | Residual crosslinker |
| 1 | 1.5 s | 10.1% by wt. | 0.0110% by wt. |
| 2 | 5.3 s | 9.2% by wt. | 0.0070% by wt. |
| 3 | 3.8 s | 8.4% by wt. | 0.0025% by wt. |

The results show that residual crosslinker and extractables pass through a minimum with increasing residence time.

Example 4

The procedure of Example 1 was repeated. The addition point of the crosslinker was 2.5 m upstream of the reactor entrance. The residence time of the crosslinker in the monomer solution upstream of the polymerization reactor was 3.8 seconds.

To meter in the crosslinker, a 93.2 cm-long Venturi tube was used (FIG. 1), in which the pipeline narrowed from a diameter of 9 cm to 3.6 cm over a distance of 8.4 cm (zone $L_1$), retained the diameter of 3.6 cm over a distance of 27.6 cm (zone $L_2$) and widened again from a diameter of 3.6 cm to 9 cm over a distance of 57 cm (zone $L_3$).

The crosslinker was metered into the Venturi tube through a pipeline having an internal diameter of 5 mm. The pipeline ended 5 cm beyond the start of the constriction zone.

The postcrosslinked polymer powder was analyzed. The results are compiled in Table 2.

Example 5

The procedure of Example 4 was repeated. The crosslinker was metered into the Venturi tube via four pipelines having an internal diameter of 5 mm. The pipelines opened 5 and 13 cm respectively beyond the start of the constriction zone. The pipelines were opposite one another in pairs. The pipe axes of the two pipeline pairs were rotated by 90° with respect to one another.

The postcrosslinked polymer powder was analyzed. The results are compiled in Table 2.

Example 6

The procedure of Example 4 was repeated. The crosslinker was metered into the Venturi tube through eight pipelines having an internal diameter of 5 mm. The pipelines opened 5 and 13 cm respectively beyond the start of the constriction zone, with four pipelines in each case at right angles to one another.

TABLE 2

| | Number of feeds | | |
| --- | --- | --- | --- |
| Example | Number of feeds | Extractables | Residual crosslinker |
| 4 | 1 | 8.0% by wt. | 0.0015% by wt. |
| 5 | 4 | 8.3% by wt. | 0.0009% by wt. |
| 6 | 8 | 8.4% by wt. | <0.0008% by wt. |

The results show that the residual crosslinker decreases with increasing number of feeds.

What is claimed is:

1. A process for continuously preparing water-absorbing polymers by mixing a monomer solution with at least one crosslinker and polymerizing a resulting mixture, wherein a residence time of the mixture between an addition of the at least one crosslinker and entry into a polymerization reactor is less than 180 seconds.

2. The process according to claim 1, wherein the residence time of the mixture between the addition of the at least one crosslinker and the entry into the polymerization reactor is at least one second.

3. The process according to claim 1, wherein the inner surface of a connection between a feed of the at least one crosslinker and the polymerization reactor at least partly has a contact angle for water of at least 60°.

4. The process according to claim 1, wherein the at least one crosslinker is not completely soluble in the mixture.

5. The process according to claim 1, wherein the mixture is inertized.

6. The process according to claim 1, wherein the at least one crosslinker is metered into a monomer solution via a Venturi tube.

7. The process according to claim 1, wherein the mixture, between the addition of the at least one crosslinker and the polymerization, flows at least partly with a velocity which corresponds to a Reynolds number of from 1000 to 10,000.

8. The process according to claim 1, wherein at least 50 mol% of the monomers of the monomer solution are acrylic acid and/or salts thereof.

9. The process according to claim 1, wherein the monomer solution is polymerized in the polymerization reactor to give a hydrogel, dried, ground, and classified.

10. The process according to claim 9, wherein the classified polymer particles are surface postcrosslinked.

11. The process according to claim 3, wherein the at least one crosslinker is metered into the monomer solution via a Venturi tube.

12. The process according to claim 11, wherein the mixture, between the addition of the at least one crosslinker and the polymerization, flows at least partly with a velocity which corresponds to a Reynolds number of from 1000 to 10,000.

13. The process according to claim 1 wherein the residence time is less than 120 seconds.

14. The process according to claim 1 wherein the residence time is less than 60 seconds.

15. The process according to claim 1 wherein the residence time is less than 10 seconds.

16. The process according to claim 1 wherein the residence time is from 1 to 5 seconds.

17. The process according to claim 1 wherein the monomer solution has a viscosity of 5 to 200 mPas at 15° C., as measured with a Brookfield viscometer (spindle 2, 100 rpm).

18. The process according to claim 1 wherein the monomer solution has a viscosity of 10 to 100 mPas at 15° C., as measured with a Brookfield viscometer (spindle 2, 100 rpm).

19. The process according to claim 1 wherein the monomer solution has a viscosity of 20 to 50 mPas at 15° C., as measured with a Brookfield viscometer (spindle 2, 100 rpm).

* * * * *

UNITED STATES PATENT AND TRADEMARK OFFICE
CERTIFICATE OF CORRECTION

| | | |
|---|---|---|
| PATENT NO. | : 7,915,355 B2 | Page 1 of 1 |
| APPLICATION NO. | : 12/065358 | |
| DATED | : March 29, 2011 | |
| INVENTOR(S) | : Matthias Weismantel et al. | |

It is certified that error appears in the above-identified patent and that said Letters Patent is hereby corrected as shown below:

Column 10, line 59, "180" should be -- 30 --.

Signed and Sealed this
First Day of May, 2012

David J. Kappos
*Director of the United States Patent and Trademark Office*